United States Patent
Andreis et al.

(10) Patent No.: US 10,471,404 B2
(45) Date of Patent: Nov. 12, 2019

(54) VALVE FOR DOSING AND MIXING FLUIDS AND RELATIVE BRIX DEGREES OPTICAL SENSOR

(71) Applicant: DOLPHIN FLUIDICS S.R.L., Corsico (MI) (IT)

(72) Inventors: Diego Andreis, Milan (IT); Francesco Butera, Arese (IT)

(73) Assignee: Dolphin Fluidics S.R.L., Corsico (MI) (IT)

( * ) Notice: Subject to any disclaimer, the term of this patent is extended or adjusted under 35 U.S.C. 154(b) by 113 days.

(21) Appl. No.: 15/805,237

(22) Filed: Nov. 7, 2017

(65) Prior Publication Data
US 2018/0126347 A1 May 10, 2018

(30) Foreign Application Priority Data
Nov. 8, 2016 (IT) .................. 102016000112087

(51) Int. Cl.
| | |
|---|---|
| *B01F 15/00* | (2006.01) |
| *B01F 15/04* | (2006.01) |
| *B01F 3/08* | (2006.01) |
| *B01F 5/00* | (2006.01) |
| *B01F 15/02* | (2006.01) |

(Continued)

(52) U.S. Cl.
CPC ........ *B01F 15/0429* (2013.01); *B01F 3/0861* (2013.01); *B01F 5/008* (2013.01); *B01F 15/026* (2013.01); *B67D 1/0022* (2013.01); *F16K 19/00* (2013.01); *F16K 31/02* (2013.01); *F16K 37/005* (2013.01); *G01N 21/43* (2013.01); *G05D 11/135* (2013.01); *G05D 11/138* (2013.01); *B01F 2215/0022* (2013.01)

(58) Field of Classification Search
CPC ........... B01F 2215/0022; B01F 3/0861; B01F 5/0429; B01F 5/008; B01F 15/026; B67D 1/0022; F16K 19/00; F16K 31/02; F16K 37/005; G01N 21/43; G05D 11/135; G05D 11/138
See application file for complete search history.

(56) References Cited

U.S. PATENT DOCUMENTS

| | | | |
|---|---|---|---|
| 3,628,867 A | 12/1971 | Brady | |
| 5,285,815 A * | 2/1994 | Henry | .................. B67D 1/0044 137/595 |

(Continued)

FOREIGN PATENT DOCUMENTS

| | | |
|---|---|---|
| CN | 204495708 | 3/2015 |
| EP | 1050753 | 8/2000 |

(Continued)

*Primary Examiner* — Anshu Bhatia
(74) *Attorney, Agent, or Firm* — King & Schickli, PLLC (57) ABSTRACT

A valve for dosing and mixing two fluids includes two respective inlet ducts, a double chamber for controlling the flows, at least one actuator configured to regulate the flow rates of the two fluids to be mixed, an electronic control unit and a Brix degrees optical sensor, arranged on the mixing duct of the mixture of the two fluids and operatively connected to the electronic control unit. The optical sensor is configured to send a measurement and control signal to the electronic control unit to drive the actuator so as to proportionally control the flow rates of the two fluids and, therefore, regulate the mixing ratio of the two fluids.

10 Claims, 8 Drawing Sheets

(51) Int. Cl.
*B67D 1/00* (2006.01)
*F16K 11/00* (2006.01)
*F16K 31/02* (2006.01)
*F16K 37/00* (2006.01)
*G05D 11/13* (2006.01)
*G01N 21/43* (2006.01)

(56) References Cited

U.S. PATENT DOCUMENTS

| | | |
|---|---|---|
| 6,135,319 A | 10/2000 | Camezon |
| 2015/0298082 A1* | 10/2015 | Machuca ............ B01F 15/0022 366/152.3 |

FOREIGN PATENT DOCUMENTS

| | | |
|---|---|---|
| GB | 2087554 | 11/1981 |
| WO | WO03107109 | 6/2003 |

* cited by examiner

VALVE FOR DOSING AND MIXING FLUIDS AND RELATIVE BRIX DEGREES OPTICAL SENSOR

This application claims the benefit of Italian Patent Application Ser. No. 102016000112087, filed Nov. 8, 2016, the disclosure of which is incorporated herein by reference.

TECHNICAL FIELD

The present invention refers in general to a valve for dosing and mixing fluids and, in particular, to an optical measurement device for controlling the mixing ratio of two fluids (which constitute, for example, the so-called soft drinks, in other words mixtures of syrup and fizzy water) integrated in a valve for dosing and mixing fluids.

BACKGROUND

In the preparation of a soft drink through the mixing of syrup and water, the refractometric technique for measuring the sugar concentration expressed in Brix degrees is widely adopted. The final quality of a soft drink is indeed highly dependent on the ratio between syrup and water.

The measurement of Brix degrees is usually carried out with an optical refractometer. An example of an optical device for detecting Brix degrees is described in document CN 204495708 U. In this device, a prism is provided the inclined faces of which are used as a mirror (total reflection) to direct the measurement beam. The device also comprises further optical elements, consisting of lenses. The detector consists of an image sensor and finally a cleaning system of the optical device is provided. The optical device described in document CN 204495708 U is therefore complex and provides for a different measurement methodology with respect to that of the sensor according to the present invention.

Another example of an optical device for detecting Brix degrees is described in document EP 1050753 A2. This optical device is expressly used for the measurement of Brix degrees in controlling the mixing ratio of soft drinks. However, the layout of the optical device described in document EP 1050753 A2 differs from that of the sensor according to the present invention, just as the respective components differ.

SUMMARY

The purpose of the present invention is therefore that of making a valve for dosing and mixing fluids, typically with at least two independent channels, which has the ability to autonomously control the mixing ratios between at least two different fluids based on optical reading of Brix degrees of the mixed fluid, using a respective sensor directly integrated in the valve itself. The sensor is provided with the following characteristics:

Measurement through the critical reflection angle technique. This measurement methodology allows a high level of miniaturisation and integration, as well as cost-effectiveness of the sensor, without excessively compromising accuracy;

measurement and consequent feedback directly in the "on line" process and in real time. The integration of sensor and valve in the same measurement and control electronics allows a high reading speed and minimum response times;

the optical sensor works in the absence of lenses, since it exploits an optical wave guide directly obtained in a single element that also forms a contact and confinement casing of the mixed fluid;

the optical wave guide and the housing system of the emitter component and of the receiver component is made in a single element able to be obtained by injection moulding, in order to ensure miniaturisation and cost-effectiveness without invalidating the precision of the measurement, as well as repeatability;

the geometry of the optical wave guide, which is also an integral part of the fluidic body, has been suitably studied in order to ensure a laminar flow that does not provide fluid stagnation areas or stagnation areas of the gas contained in the fluid (like for example $CO_2$ for carbonated drinks) which can compromise the reliability and repeatability of measurement.

The aforementioned purpose according to the present invention is accomplished by making a valve for dosing and mixing fluids and a relative Brix degrees optical sensor as outlined in claim 1.

Further characteristics of the invention are highlighted by the dependent claims, which are an integral part of the present description.

In general, the mixing ratio can be controlled based on the measurement of concentration of a substance in a fluid, on which the refraction index of the mixture formed depends. Based on such a ratio, measured by the optical sensor of the valve according to the present invention, it is possible to regulate the flow rate of the two channels of the valve in a closed loop, so as to regulate the concentration of the mixture. Such control is particularly required both in the "beverage" industry, where it is necessary to maintain certain ratios between syrup and water to correctly prepare drinks, and in other fields, like for example medicine, where it is necessary to dose drugs or substances in physiological solutions maintaining the ratios in a very precise manner. The valve according to the present invention is thus intended in particular for the preparation of soft drinks, without however thereby limiting the use of the valve itself in other fields.

The optical sensor of the valve according to the present invention proposes to identify the final quality of a soft drink through an on-line measurement in real time of Brix degrees at the outlet of the valve itself, whether or not there are bubbles due to the carbonisation of the water. The valve according to the present invention also makes it possible, again through the on-line measurement of Brix degrees, to identify what type of drink is being prepared, being able to distinguish through the signal of the sensor the type of mixture of syrup and water in preparation. For this reason, for example, it can be understood whether a cola or orange-flavoured drink is being prepared, as well as what specific brand of syrup is being used. This data can be used not only to optimise the quality of the drink, but also as anti-fraud signal or as statistical data for commercial and marketing purposes.

The valve according to the present invention is provided in particular with a fitting that combines the two outputs of the two channels in a single channel where the Brix degrees optical sensor is placed. The sensor is configured to send a measurement and control signal to an electronic control unit that, with suitable processing of such a measurement and control signal, will drive the actuator of the valve so as to proportionally control the flow rate of the two channels and, therefore, regulate the mixing ratio based on the desired drink. The measurement and control signal sent by the sensor, moreover, is made available by the electronic control unit towards the outside and can be transmitted in a wired or wireless manner to any local or remote data collection system.

BRIEF DESCRIPTION

The characteristics and advantages of a valve for dosing and mixing fluids and of a relative Brix degrees optical sensor according to the present invention will become clearer from the following description, given as an example and not for limiting purposes, referring to the attached schematic drawings, in which.

DETAILED DESCRIPTION

Figure 11:
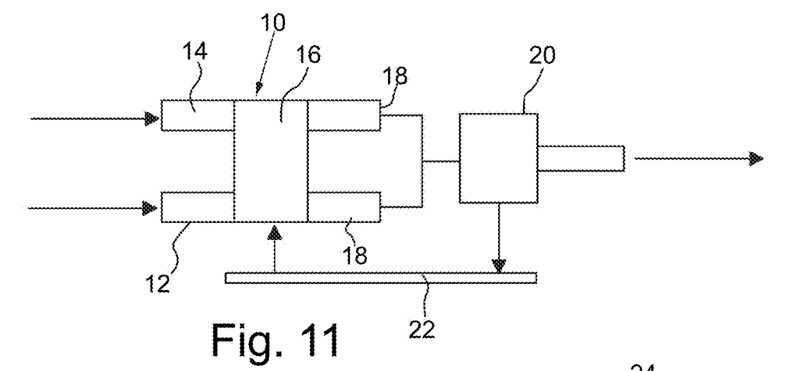
FIG. 11 is a schematic view of the valve for dosing and mixing fluids and of the relative Brix degrees optical sensor according to the present invention.
Figure 12:
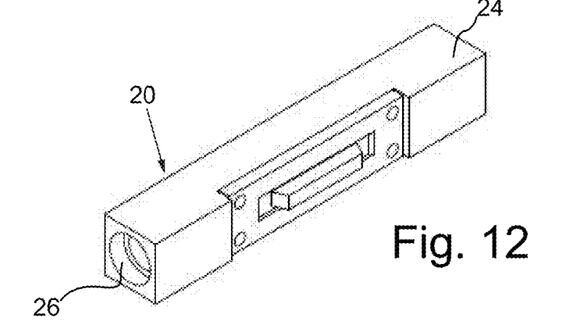
FIG. 12 is a perspective view of the measurement cell of the Brix degrees optical sensor according to the present invention.

With reference to the figures, a valve for dosing and mixing fluids according to the present invention is shown, wholly indicated with reference numeral 10. The valve 10 comprises at least one first inlet duct 12 for at least one first fluid to be mixed, which can for example consist of a syrup. The valve 10 also comprises at least one second inlet duct 14 for at least one second fluid to be mixed, which can for example consist of carbonated or still water.

The first inlet duct 12 and the second inlet duct 14 are provided with at least one actuator (not shown) configured to regulate the flow rates of the first fluid to be mixed and of the second fluid to be mixed that respectively flow in the first inlet duct 12 and in the second inlet duct 14.

The valve 10 comprises a double chamber 16 for controlling flows. Downstream of the double chamber 16 for controlling flows at least one mixing duct 18 is arranged where the flows of the respective first inlet duct 12 and second inlet duct 14 are placed in fluid communication. In particular, the valve 10 is provided with two mixing ducts 18 and with a fitting that joins the two outlets of such two mixing ducts 18 in a single channel where the optical sensor 20 of Brix degrees is arranged.

The optical sensor 20 is configured to send a measurement and control signal to an electronic control unit 22 that, with suitable processing of such a measurement and control signal, drives the actuator of the valve 10 so as to proportionally control the flow rates of fluid that respectively flow in the first inlet duct 12 and in the second inlet duct 14 and, therefore, regulate the mixing ratio of the first fluid and of the second fluid based on the desired drink. The electronic control unit 22 can be provided with a communication system, wired or wireless, configured to make the measurement and control signal sent by the optical sensor 20 available towards the outside.

For the purposes of the present invention two possible methodologies for the measurement, through the optical sensor 20, of the refraction index of the mixture of the first fluid and of the second fluid have been analysed. A first methodology is essentially linked to the intensity of an optical signal reflected by normal incidence at the solid-liquid interface. The second methodology is linked to the angular position of the beam detected around the total internal reflection critical angle at the solid-liquid interface. Four different plastic materials compatible with optical applications have also been considered. From the analysis of simulations, it has been worked out that the measurement of the critical angle is preferable with respect to the measurement by normal incidence for three main reasons:

because it allows the normalisation of the optical signal with respect to the variations of intensity of the source of such a signal with a scheme that is simple to implement;

because the characteristics of sensitivity of the optical sensor 20 can be optimised by acting on geometric parameters of the measurement methodology;

for the same optical signal emitted by the source, the signal intensity useful for measurement is higher.

Figure 1:
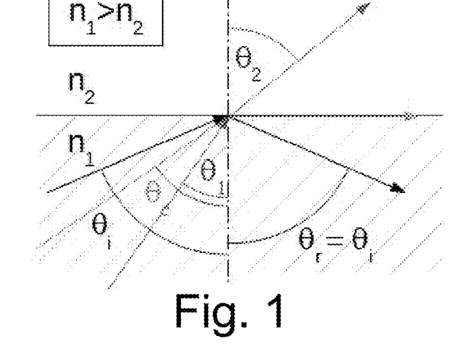
FIG. 1 shows the total internal reflection critical angle at the interface between a solid and a liquid having refraction index $n_1$ and $n_2$, wherein $n_1 > n_2$.

Considering that the mixing valve 10 in which it is provided for to integrate the optical sensor 20 for measuring the quality of the soft drink is preferably made of plastic material, it is possible to use the light propagation characteristics at the interface between the two media, in other words the plastic material with known refraction index and the soft drink with refraction index object of measurement, to determine the concentration of sugar in solution. FIG. 1 indicates the effects of the propagation at the interface between two media with refraction index $n_1$ and $n_2$, in which $n_1 > n_2$. In this specific case the following applies:

$$n_1 = n_{plastic} = 1.57;$$

$n_2 = n_{softdrink} = 1.35$.

There is therefore an angle of incidence at the interface whereby the phenomenon of total internal reflection occurs (critical angle θ), which can be exploited to evaluate the variation of intensity of the light reflected in a certain position, as a function of the variation of refraction index $n_2$ (FIG. 1). In reality, the reflection coefficient by normal incidence at the interface also provides a measurement of $n_2$, which could translate into a very simple embodiment of the optical sensor 20 of the valve 10 according to the present invention, even if probably with lower resolution, or into a tool for evaluating possible ageing effects of the plastic material of the valve 10 itself.

The choice of the measurement methodology to be implemented in making the optical sensor 20 depends, as well as of course on the respect of the measurement specifications, also on other factors, like for example:
  simplicity and low cost;
  compatibility with the space occupied by the mixing valve 10;
  integrability of the optical parts in the mould of the casing 24 of the optical sensor 20.

The optical sensor 20 is indeed made in the form of a casing 24 on which inlet/outlet surfaces of the optical signal are obtained, as shown for example in the scheme of FIG. 3 and as will be specified better hereinafter. The casing 24 is provided with an inlet duct 26 for the mixture of the first fluid and of the second fluid exiting from the valve 10, as well as with an outlet duct 28 for mixing the first fluid and the second fluid exiting from the optical sensor 20. The presence of inlet 26 and outlet 28 ducts of the mixture of fluids makes it possible to carry out the analysis on the fluid in motion. Of course, the optical sensor 20 can be an integral part of the mixing valve 10.

Figure 15:
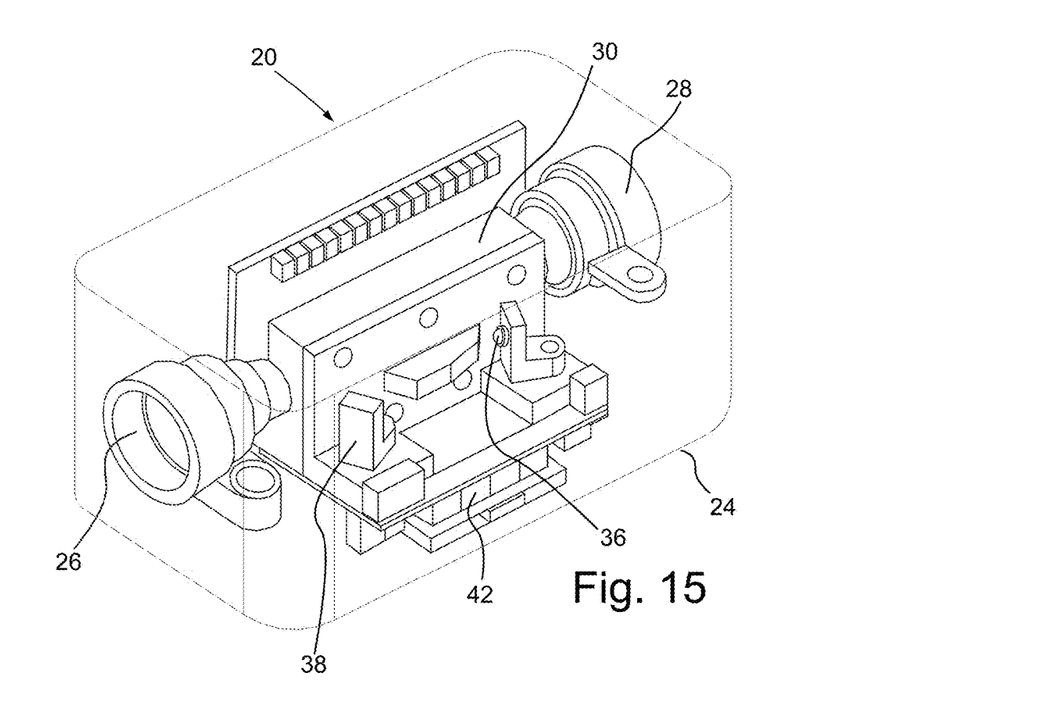
FIG. 15 is a transparent view of the Brix degrees optical sensor according to the present invention.

As shown in FIG. 15, between the inlet duct 26 of the mixture of fluids and the outlet duct 28 of the mixture of fluids a measurement chamber 30 passed through by the flow of such a mixture of fluids is arranged. In detail, the measurement chamber 30 is provided with a passive portion, consisting of a pipe 32 that places the inlet duct 26 of the mixture of fluids and the outlet duct 28 of the mixture of fluids in communication, and with an active portion, comprising a measurement optical prism 34, an emitter device 36 of the optical signal and a receiver device 38 of the optical signal.

The measurement optical prism 34 has the function of a wave guide of the optical signal emitted by the emitter device 36 and received by the receiver device 38. The measurement optical prism 34 is made integral with a surface 40 that faces the pipe 32 and that constitutes the solid-liquid interface, wherein the solid medium consists of a polymer or glassy material from which the surface 40 itself is manufactured, whereas the liquid medium consists of the mixture of fluids for which it is intended to measure the Brix degrees.

The active portion of the measurement chamber 30 also comprises an electronic board 42 for conditioning the optical signal, directly interfaced with the electronic control unit 22 of the valve 10. Between the active portion and the passive portion of the measurement chamber 30 and, more precisely, between the pipe 32 and the surface 40 of solid-liquid interface a gasket 44 is arranged that ensures the seal between such an active portion and such a passive portion of the measurement chamber 30.

Figure 16:
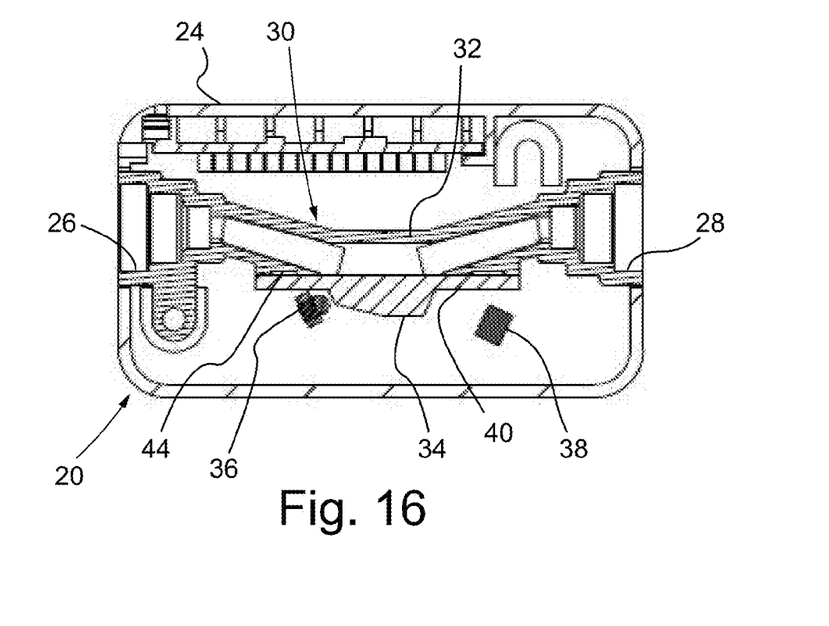
FIG. 16 is a section view of the optical sensor of FIG. 15.

From the section view of FIG. 16 it can be seen how the active portion of the measurement chamber 30, which comprises the measurement optical prism 34 and the housings of the optically active parts, in other words the emitter device 36 and the receiver device 38, is made as an en bloc that also constitutes part of the passive portion of the measurement chamber 30, in other words the pipe 32 in which the mixture of fluids flows. Again, from the section view of FIG. 16 it can be seen how the pipe 32 has a substantially V-shaped longitudinal section, with the vertex of the V arranged at the surface 40 of solid-liquid interface. This oblique conformation of the pipe 32 with respect to the surface 40 placed in contact with the mixture of fluids avoids the formation of fluid stagnation areas, as well as gas bubble formation sacks, which can jeopardise the quality of the measurement.

Figure 17:
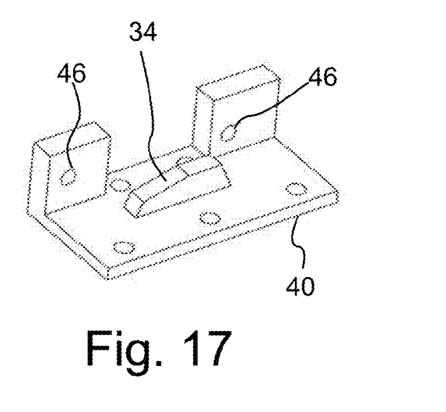
FIG. 17 is a detailed view of a component of the optical sensor of FIG. 15.
Figure 18:
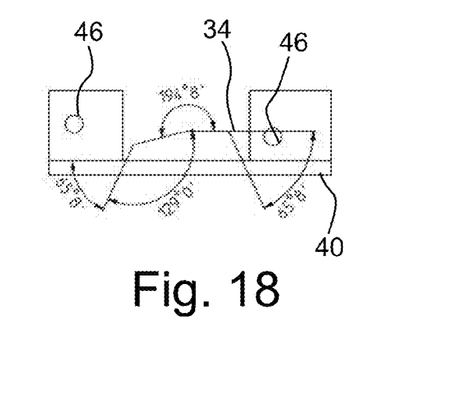
FIG. 18 is a side elevation view of the component of FIG. 17.

FIGS. 17 and 18 show in detail the component that integrates the functions of measurement optical prism 34, or optical wave guide, surface 40 of solid-liquid interface and holes 46 for housing the emitter device 36 and the receiver device 38. The specific geometry of the measurement optical prism 34 and the relative constructive angles, illustrated in FIG. 18, have been optimised in order to exploit the maximum possible resolution around the critical angle of interest and in relation to the miniaturised design of the entire optical sensor 20.

Figure 2:
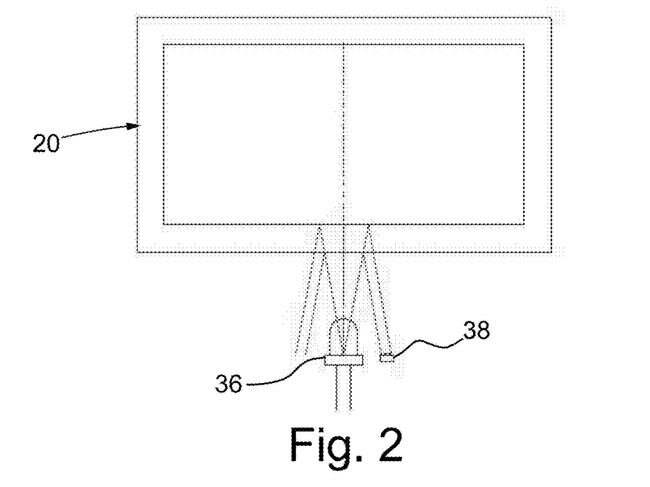
FIG. 2 is a schematic view of the optical measurement device of the present invention, configured to operate according to the measurement methodology of partial reflection by normal incidence at the solid-liquid interface.
Figure 3:
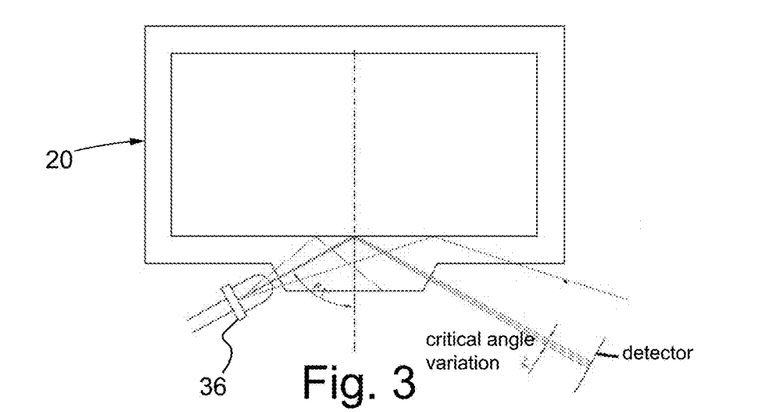
FIG. 3 is a schematic view of the optical measurement device of the present invention, configured to operate according to the measurement methodology of total internal reflection critical angle.

Hereinafter a comparison between the calculations carried out with different materials for the optical part of the sensor 20 will be given, considering two optical measurement methodologies:
  measurement of the partial reflection by normal incidence at the surface 40 of solid-liquid interface (polymer-fluid, see FIG. 2);
  measurement of the total internal reflection critical angle (FIG. 3).

It should be noted that the first is essentially an intensity measurement, whereas the second is an angular position measurement. This second measurement methodology has some advantages, including greater simplicity of normalisation of the optical signal with respect to the variations of intensity of the emitter device 36, thanks to an easier positioning of the components, and the possibility of acting on the geometric parameters of the optical sensor 20 to optimise the performance thereof (the greater the measurement distance, the better the angular sensitivity).

For the optical part of the sensor 20 five possible materials are considered, including four polymeric materials, which have optical characteristics compatible with the measurement requirements, in order to size the sensor 20 itself and evaluate the performance thereof as a function of the refraction index:
  PMMA: acronym of polymethylmethacrylate, polymer also known as Plexiglas (for example Lucite Diakon®), ideal for producing optical fibres due to its excellent transmission characteristics, with refraction index n=1.49;
  COC: acronym of cyclic olefin copolymer or "cyclic olefin copolymer", produced by Mitsui Chemicals (APEL™) and used to manufacture optical devices, with refraction index n=1.54;
  PC: acronym of polycarbonate, polymer available in different variants (for example LEXAN™), also used to manufacture optical devices, with refraction index n=1.58;
  PSU: acronym of polysulfone, high-strength transparent material, produced by Solvay with the trade name UDEL®, with refraction index n=1.63;
  glass.

Hereinafter the two different measurement methodologies cited above are considered: normal incidence and angled incidence with respect to the surface 40 of solid-liquid interface. The measurement of the reflection coefficient by normal incidence to the surface 40 of solid-liquid interface (polymer-fluid) is the simplest of the optical measurement methodologies. In this measurement methodology, a separation surface between the polymer and the fluid is used to measure the variation of intensity reflected at the respective interface and, from this, obtain a measurement of the refraction index of the fluid.

Figure 4:
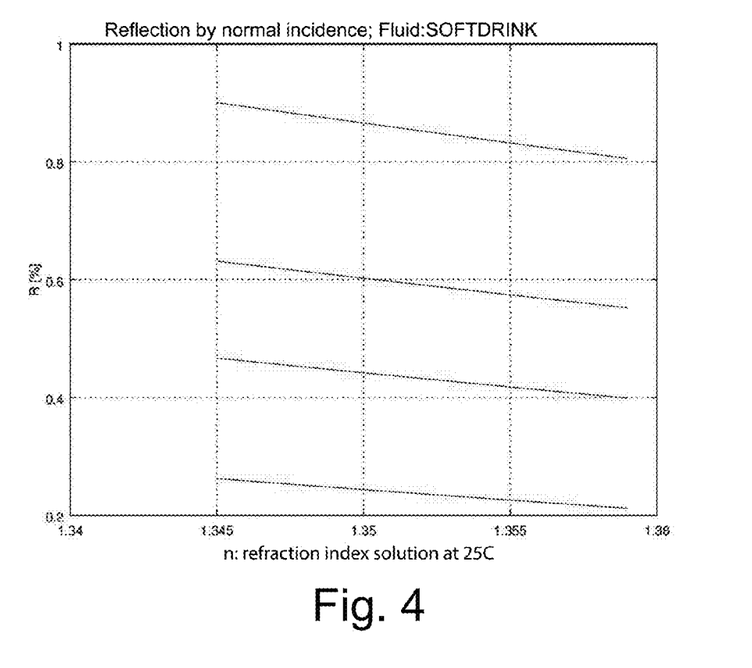
FIG. 4 is a graph that shows the reflectivity curves by normal incidence at the interface between a fluid (soft drink) and a polymeric material for different types of polymeric materials.
Figure 5:
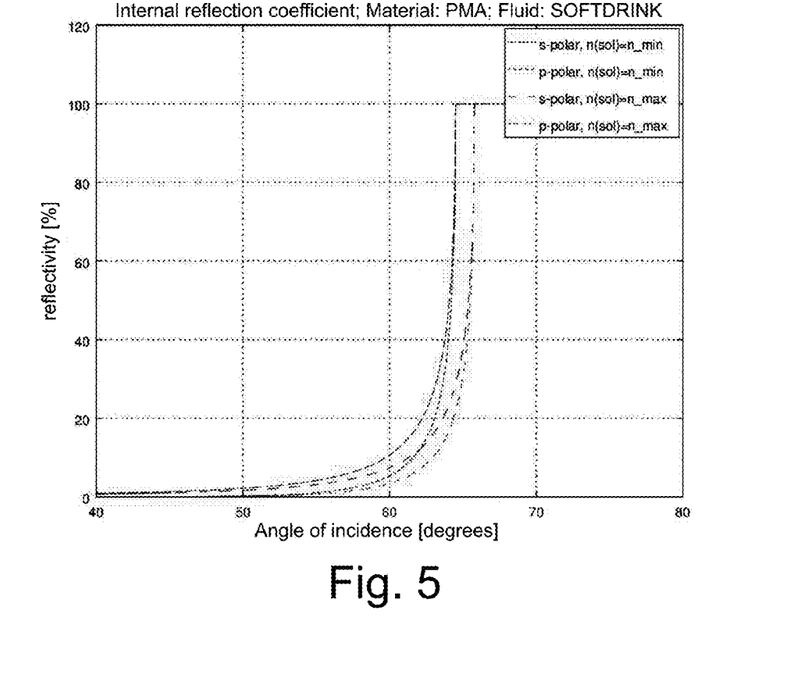
FIGS. 5 to 8 show respective graphs of the reflectivity coefficients at the interface between the polymeric materials considered and the fluid in the two mixing conditions at the extremes of the range of interest, for two different polarisation states of the light, wherein the states p and s respectively correspond to the light parallel and perpendicular to the plane of incidence.
Figure 6:
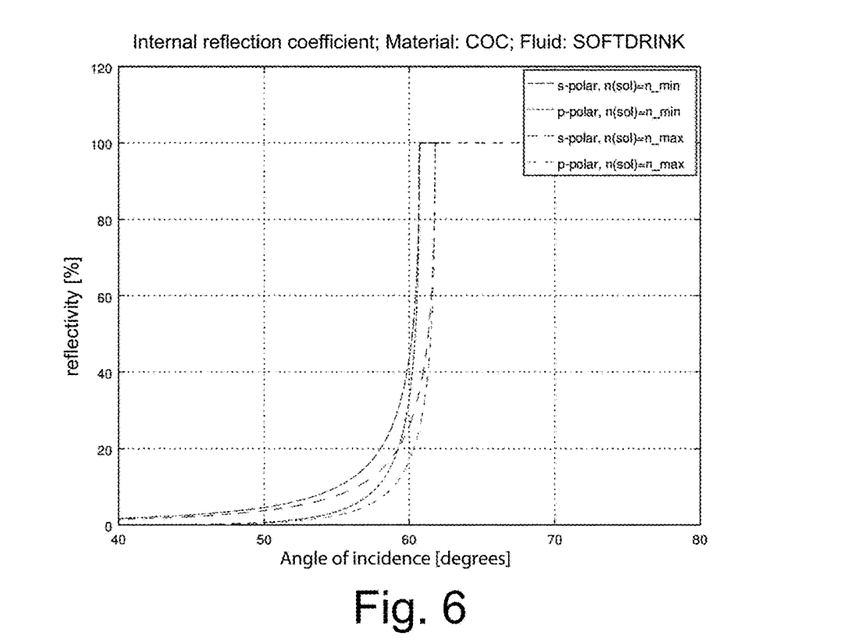
Figure 7:
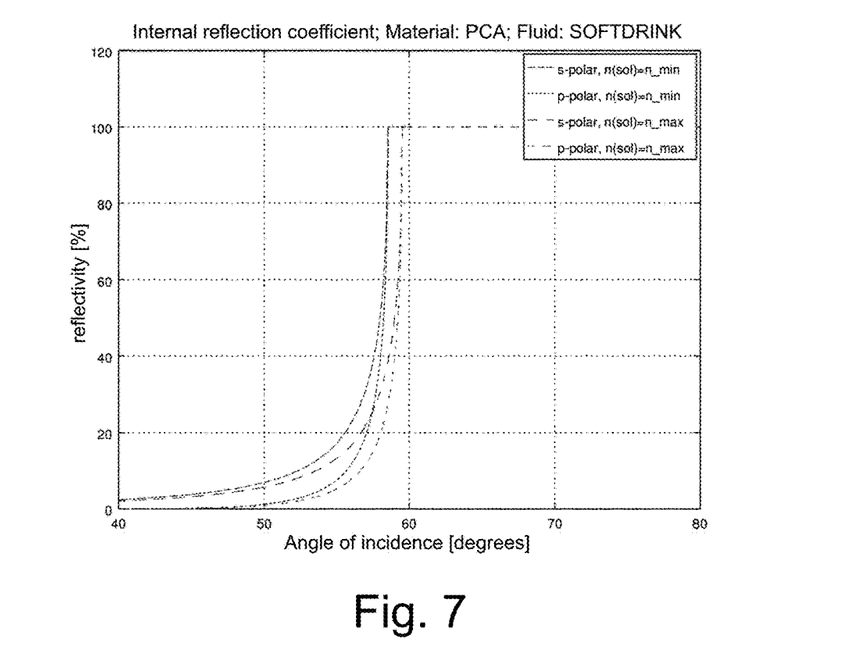
Figure 8:
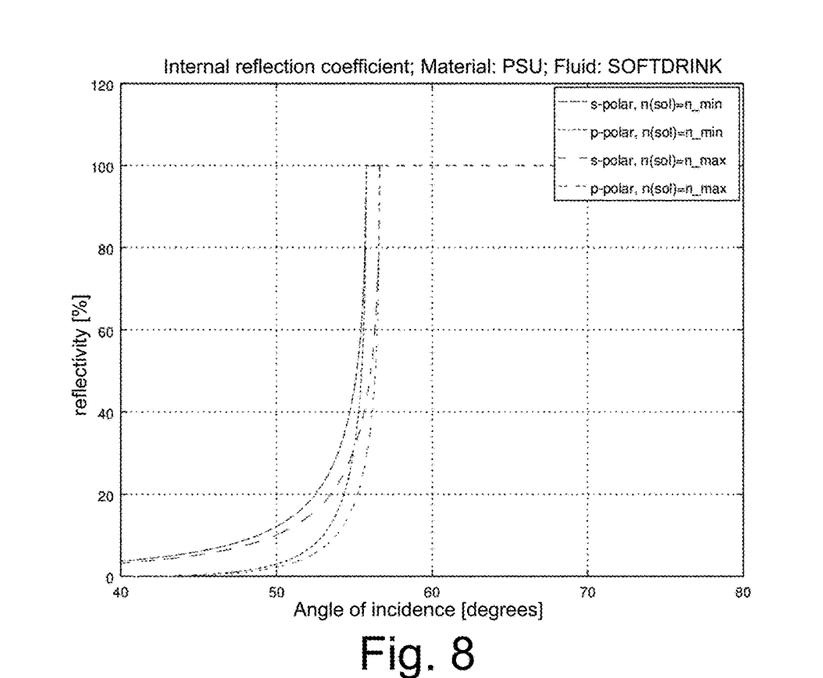

From the comparison between the curves of FIG. 4 it can be seen that a greater jump of the refraction index between the polymer and the sugar solution promotes the measurement. Indeed, both the average reflectivity by normal incidence to the surface 40 of solid-liquid interface, and its variation with the refraction index of the soft drink are greater in the case of PSU and progressively decrease for PC, COC and PMMA. However, the reflectivity by normal incidence is very low. In the best case of PSU it goes roughly from 0.8% to 0.9%, considering the variation of the refraction index of the soft drink for the entire field of interest from 7 to 15 Brix degrees, thus having a very small fraction of the incident optical signal available to carry out the measurement. This, against a simplicity of embodiment that could appear advantageous, results in objective difficulty in carrying out a measurement with the required resolution, which is kept stable over time and is as immune as possible from environmental disturbances, deterioration of the materials, of the emitter device 36 of the optical signal and so on. As stated earlier, indeed, the required measurement resolution provides for having to evaluate variations of the refraction index equal to n=0.00014 about a nominal value of such a refraction index n equal to about 1.35. Detecting variations of concentration of 5% (0.5 Brix degrees) therefore means evaluating variations of the refraction index on the fourth or fifth decimal place, in other words measuring variations of reflectivity of the order of $1/10000$.

Another notable aspect concerns the disturbance caused by the light transmitted at the surface 40 of solid-liquid interface and refracted by the fluid. This light coincides with the almost totality of the optical signal emitted by the emitter device 36, which can be diffused by the fluid or reflected by the walls of the measurement chamber 30 of the optical sensor 20 and, particularly, by the fluid-air interface at the bubbles. An interesting aspect linked to this type of measurement concerns the fact that its simplicity of embodiment makes it possible to implement a measurement of the refraction index of the polymer at the air-solid interface (reflectivity of about 4.5%) to take into account possible ageing phenomena.

In the measurement of the total internal reflection critical angle the jump of the refraction index between polymer and liquid determines a dependence on the angle of incidence of the reflection coefficient at the interface. The more the incidence grazes the surface 40, the higher the percentage of light reflected. If the refraction index of the solid is greater than that of the liquid, there is a limit angle of incidence (critical angle) beyond which there is total reflection. FIGS. 5 to 8 represent the graphs of the reflectivity coefficients at the interface 40 between the polymeric materials considered and the fluid in the two mixing conditions at the extremes of the range of interest, for two different states of polarisation of light, in which the states p and s respectively correspond to the light parallel and perpendicular to the plane of incidence. The light incident on the receiver device 38 of the optical sensor 20 consists of a combination of the two states. It should be noted that the variation of the critical angle (distance between the two pairs of curves) is a function both of the refraction index of the medium object of measurement, and of that of the optical part of the sensor 20. In particular, as the refraction index of the polymer increases, both the critical angle (incident beam that is less grazing to the surface 40), and the sensitivity of the optical sensor 20 (distance between the curves corresponding to the extremes of the range of interest) decrease.

Figure 9:
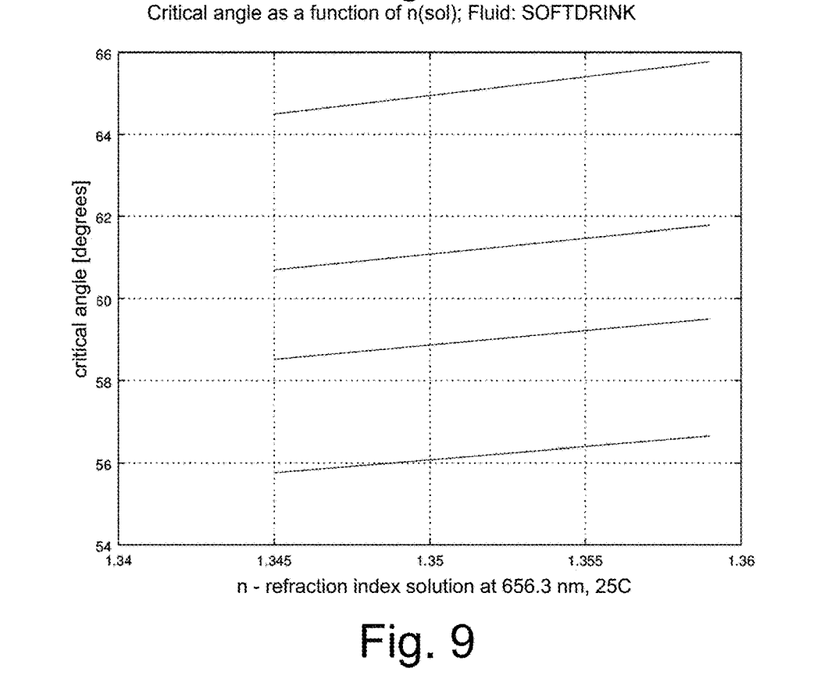
FIG. 9 is a graph that shows the curves of critical angle as a function of the refraction index for different types of polymeric materials.

In FIG. 9 this linear dependence for all of the materials considered is shown. Contrary to what was valid for the measurement of intensity of reflected light by normal incidence, whereby the greater refraction index of PSU appears advantageous, here it should be noted that materials with lower refraction index are more effective in a critical angle measurement. The variation of critical angle (and therefore the sensitivity of the optical sensor 20) is indeed greater for the material with lower refraction index: almost 1.3 Brix degrees for PMMA against about 0.8 Brix degrees for PSU. Although the difference noted is not such as to prevent the use of materials with higher refraction index, this evaluation constitutes a design criterion that tends towards polymers with lower refraction index, except that the choice is not conditioned by other reasons like availability, cost, processability of the material, ageing characteristics, etc.

The measurement of the critical angle represents the classical measurement methodology of the refraction index implemented in commercial refractometers. It consists of evaluating the angle beyond which the intensity emitted by an optical source is totally reflected towards the detector. It is thus possible to identify two easily recognisable areas, illuminated in a very different way (high intensity-low intensity) in the border region around the total internal reflection critical angle. By identifying the critical angle in the nominal conditions of use of the valve 10 (nominal concentration value at average operating temperature) it is therefore possible to identify the main directions along which to position the emitter device 36 and the receiver device 38 of the optical sensor 20 to carry out the measurement of interest. It is advantageous to make a prototype in which the inlet surface and the outlet surface of the light from the plastic material are perpendicular to these directions, to minimise the influence of the refraction at the air-solid surface and instead consider only the effect at the surface 40 of solid-liquid interface.

A relevant characteristic of this type of measurement, which makes it preferable to all others, is that the critical angle depends only on the material and is not influenced by angular positioning errors of the emitter device 36 or of the receiver device 38 of the optical signal. The measurement can also be made immune from possible fluctuations of intensity of the incident optical signal and from phenomena of degeneration of the emitter device 36.

Figure 10A:
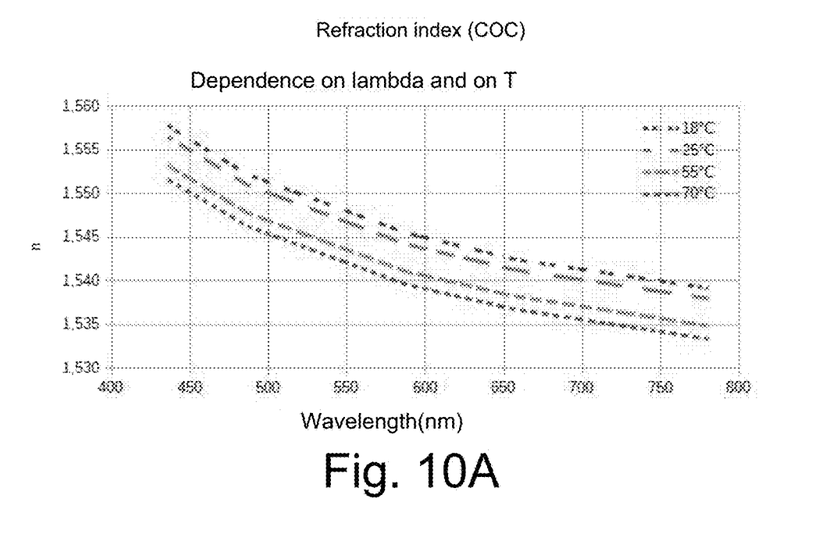
FIGS. 10A and 10B show the characteristics of dependency of the refraction index on wavelength and on temperature for a certain polymeric material (COC)
Figure 10B:
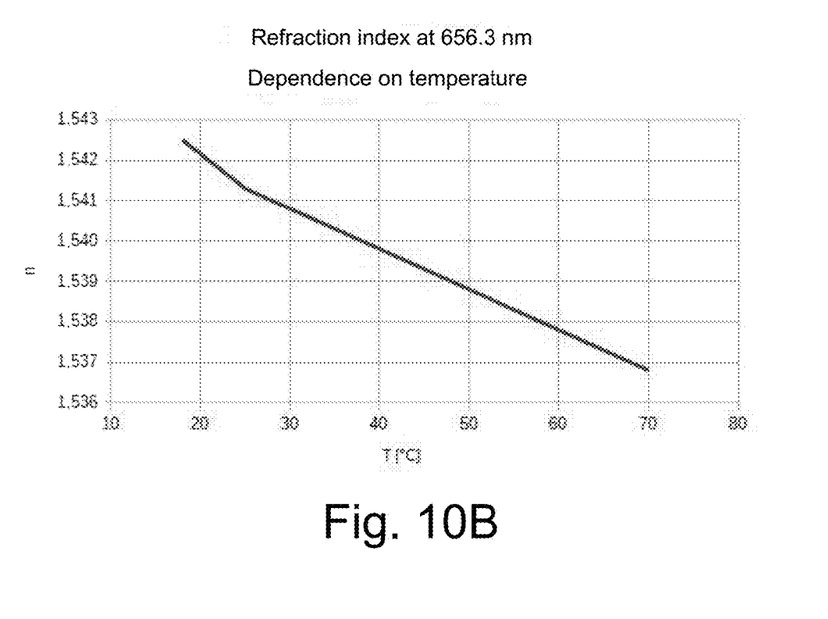

Irrespective of the measurement methodology, such a measurement is nevertheless influenced by thermal effects, due to the dependence on the temperature of the refraction index of the material. FIGS. 10A and 10B represent, as an example, the characteristics of dependency of the refraction index on the wavelength and on the temperature for COC. A similar dependence is also valid for the other materials and presumably also for the sugar solution, but the fluid is not optically characterised with this level of detail, which makes it necessary to rely on experimental data.

The dependence of the refraction index on wavelength is very weak and the choice of the operative wavelength is therefore dictated by other factors, such as the availability of the emitter device 36, the sensitivity of the receiver device 38, the cost and the simplicity of use (visible light allows easier alignment of the components with respect to infrared radiation over 700 nm). The dependence on temperature can, on the other hand, be such as to justify a compensation of the effect. Indeed, it should be noted from the graph relative to the wavelength of 656.3 nm (FIG. 10B) that a temperature variation of the order of 10° C. results in an index variation on the third decimal place, i.e. greater than the measurement resolution that it is wished to obtain, but it should be considered that the dispensing of the drink generally takes place at controlled temperature.

Based on the experimental data outlined above an optical sensor 20 has been made provided with an optical part manufactured from polymethylmethacrylate (PMMA) and configured to operate according to the measurement methodology of total internal reflection critical angle, in other words with a measurement solution of the angular type like the one schematised in FIG. 3. The layout of the optical sensor 20, optimised for the various polymeric materials taken into consideration, provides that the angled input-output faces of the optical signal form an angle comprised between 40° and 80° with respect to the wall of the casing 24. The measurement optical prism 34 can also have a wave guide function, so as to take the optical signal from the emitter device towards the receiver device 38, both physically housed on a single plane of the electronic board 42 for conditioning the optical signal itself. The angled input-output faces of the optical signal must have sufficient optical quality for the transmission of such an optical signal without significant diffusion and distortion effects. The dimensions of the casing 24 must also allow easy positioning and adjustment of the alignment of the emitter device 36 and of the receiver device 38.

The presence of the inlet 26 and outlet 28 ducts of the mixture of fluids controlled by the mixing valve 10 makes it possible to carry out measurements in the presence of flow. This aspect is decisive to evaluate the actual possibility of averaging the measurements both spatially, and temporally to minimise the disturbance caused by bubbles and turbulence. The optical sensor 20 is operatively connected with the electronic control unit 22, which is capable of driving the emitter device 36 of the optical signal and is provided with analogue outlets for reading the measurement and control signal.

The optical sensor 20 has been subjected to dynamic tests with different mixtures. A first test was carried out with a mixture consisting of fizzy water added to with a cola syrup, dosed at successive intervals of 1 ml at a time in 500 ml of water. The test was repeated many times to evaluate the disturbance elements. Already in the first attempt it was noted that the effect of spatial and temporal averaging, obtained thanks to the flow of the mixture, makes the presence of the bubbles substantially irrelevant, which is absolutely positive as a function of the application of the optical sensor 20 on a valve 10 for dispensing a drink. It was also noted that there was a slight dependence of the measurement on the temperature and on the feeding speed of the mixture and it was also noted that the value measured with the mixture of water and cola syrup, at the nominal concentration (about 4.1%), does not correspond to that detected with another type of cola syrup, denoting a dependence of the measurement on the type of drink.

Figure 13:
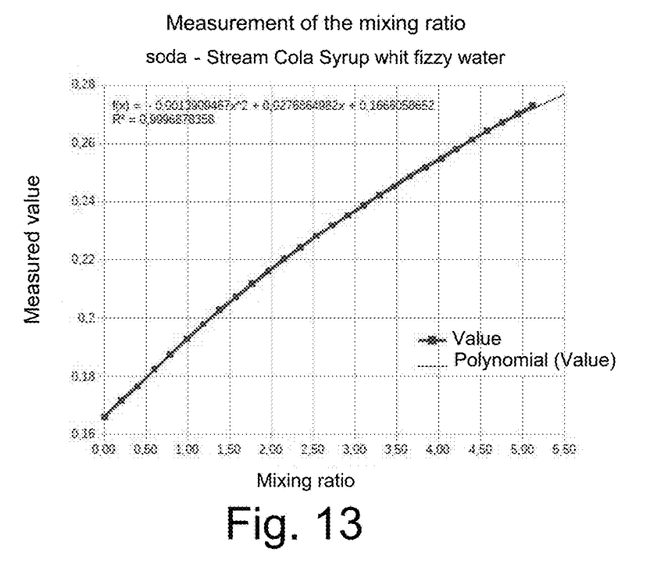
FIG. 13 is a graph that shows the measurement of Brix degrees in a soft drink as a function of the mixing ratio, wherein the two mixed fluids consist of a cola syrup and carbonated water.
Figure 14:
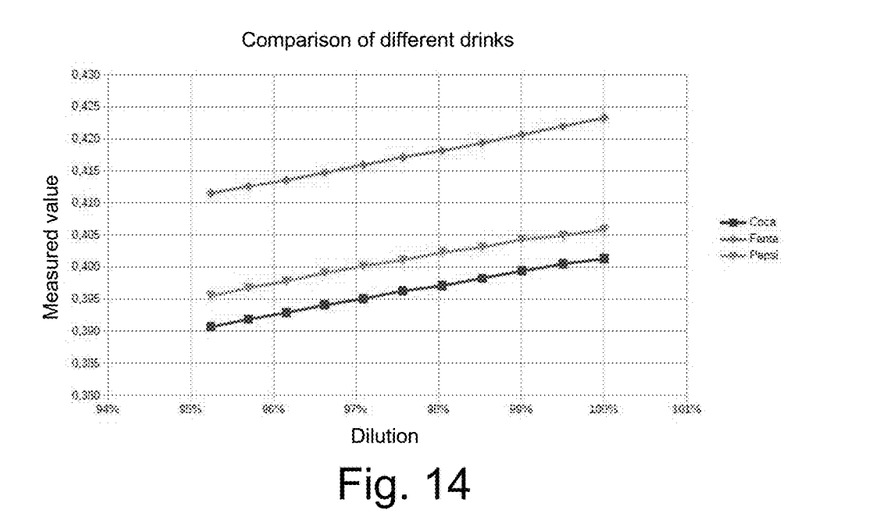
FIG. 14 is a graph that shows the measurement of Brix degrees in a plurality of commercial drinks as a function of the percentage dilution.

The results of the tests were satisfactory, as highlighted by the graphs of FIGS. 13 and 14. The regularity of the curves and the low noise level of the signal allow a resolution of concentration measurement of syrup in water better than 1 ml/l. In particular, around the nominal concentration the optical sensor 20 shows a sensitivity of about 3 mV/ml, as shown by the curve of FIG. 13.

Since it was found that there was a difference of the value measured with drinks based on two different types of cola syrup, a comparison of the characteristics obtained with different commercial products was carried out, starting from the pure drink and diluting it gradually with fizzy water, shifting a little away from the nominal concentration. The graphs of FIG. 14 show that, for the same concentration and limited to the products tested, the measurement of refraction index makes it possible to distinguish the drink at the dispenser.

It has thus been seen that the valve for dosing and mixing fluids and the relative Brix degrees optical sensor according to the present invention achieve the purposes highlighted earlier.

The valve for dosing and mixing fluids and the relative Brix degrees optical sensor of the present invention thus conceived can in any case undergo numerous modifications and variants, all of which are covered by the same inventive concept; moreover, all of the details can be replaced by technically equivalent elements. In practice, the materials used, as well as the shapes and sizes, can be whatever according to the technical requirements.

The scope of protection of the invention is therefore defined by the attached claims.

The invention claimed is:

1. Valve for dosing and mixing fluids comprising:
   at least one first inlet duct for inletting at least one first fluid to be mixed;
   at least one second inlet duct for inletting at least one second fluid to be mixed;
   a double chamber for controlling the flows placed in fluid communication with the first inlet duct and with the second inlet duct;
   at least one actuator configured to regulate the flow rates of the first fluid to be mixed and of the second fluid to be mixed, which flow in the first inlet duct and in the second inlet duct respectively;
   at least one mixing duct for mixing the mixture of fluids, placed downstream of the double chamber for controlling the flows;
   an electronic control unit for controlling the valve; and
   a Brix degree optical sensor, placed on the mixing duct for mixing the mixture of fluids and operatively connected to the electronic control unit, said optical sensor being configured to send a measurement and control signal to said electronic control unit, which drives said actuator so as to proportionally control the fluid flow rates flowing in the first inlet duct and in the second inlet duct respectively, and, thus, to regulate the mixing ratio of the first fluid and of the second fluid,
   wherein the optical sensor is made in the shape of a casing provided with a third inlet duct for mixing the first fluid and the second fluid exiting from the valve, as well as with an outlet duct for mixing the first fluid and the second fluid exiting from the optical sensor, and wherein a measurement chamber is interposed between the third inlet duct of the optical sensor and the outlet duct of the optical sensor, said measurement chamber being provided with a plurality of optical components arranged to perform the optical reading of the Brix degrees directly on the flow of the mixture of fluids passing through said measurement chamber.

2. Valve according to claim 1, characterised in that it comprises two mixing ducts and a fitting that joins the two outlets of said two mixing ducts in a single channel, said optical sensor being placed on said channel.

3. Valve according to claim 1, characterised in that the measurement chamber is provided with a passive portion, comprising of a pipe that puts in communication the inlet duct for inletting the mixture of fluids and the outlet duct for outletting the mixture of fluids, and with one active portion, comprising a measurement optical prism, an optical signal emitter device and an optical signal receiver device, wherein said measurement optical prism performs the guiding of the wave of the optical signal emitted by the emitter device and received by the receiver device.

4. Valve according to claim 3, characterised in that the active portion of the measurement chamber comprises respective housings for housing the emitter device and the receiver device and is made as an en bloc that also constitutes a part of the passive portion of the measurement chamber, namely the pipe in which the mixture of fluids flows.

5. Valve according to claim 3, characterised in that the measurement optical prism is made integral with a surface that faces the pipe and that constitutes the interface between a solid medium and a liquid medium, wherein the solid medium consists of a polymer or glassy material which said surface is made of, whereas the liquid medium consists of the mixture of fluids of which the Brix degrees are intended to be measured.

6. Valve according to claim 5, characterised in that said material is selected in the group consisting of:
polymethylmethacrylate (PMMA);
cyclic olefin copolymer (COC);
polycarbonate (PC);
polysulfone (PSU);
glass.

7. Valve according to claim 5, characterised in that the pipe has a substantially V-shaped longitudinal section, with the vertex of the V placed at the surface of the solid-liquid interface, the oblique conformation of the pipe with respect to said surface avoiding the formation of fluid stagnation areas that may affect the quality of the measurement.

8. Valve according to claim 5, characterised in that between the active portion and the passive portion of the measurement chamber and, more precisely, between the pipe and the surface of solid-liquid interface a gasket is interposed, which performs the seal between said active portion and said passive portion of the measurement chamber.

9. Valve according to claim 3, characterised in that the active portion of the measurement chamber further comprises an electronic board for conditioning the optical signal, directly interfaced with the electronic control unit of the valve.

10. Valve according to claim 1, characterised in that the electronic control unit is provided with a communication system, wired or wireless, arranged to make the measurement and control signal sent by the optical sensor available to the outside.

* * * * *